United States Patent [19]
Tuloup et al.

[11] Patent Number: 6,077,972
[45] Date of Patent: Jun. 20, 2000

[54] CERAMIDE COMPOUND, PROCESS OF PREPARATION AND USE

[75] Inventors: Rémy Tuloup, Paris; Michel Philippe, Wissous, both of France

[73] Assignee: L'Oreal, Paris, France

[21] Appl. No.: 09/185,628

[22] Filed: Nov. 4, 1998

[30] Foreign Application Priority Data

Nov. 4, 1997 [FR] France .................................. 97 13844

[51] Int. Cl.⁷ ...................... C07C 275/10; C07C 273/00; C07C 229/06
[52] U.S. Cl. .............................. 564/60; 556/12; 560/169; 560/170
[58] Field of Search ............................. 564/60; 560/169, 560/170; 556/12

[56] References Cited

U.S. PATENT DOCUMENTS

| | | | |
|---|---|---|---|
| 4,111,683 | 9/1978 | Singer | 564/60 |
| 5,198,470 | 3/1993 | Zysman et al. | |

FOREIGN PATENT DOCUMENTS

| | | |
|---|---|---|
| 0 278 505 | 8/1988 | European Pat. Off. . |
| 0 383 024 | 8/1990 | European Pat. Off. . |
| 0 420 722 | 4/1991 | European Pat. Off. . |
| 0 500 437 | 8/1992 | European Pat. Off. . |
| 0 647 617 | 4/1995 | European Pat. Off. . |
| 1 477 048 | 4/1967 | France . |
| 2 091 516 | 1/1972 | France . |
| 2 315 991 | 1/1977 | France . |
| 2 465 780 | 3/1981 | France . |
| 2 482 128 | 11/1981 | France . |
| 2 703 185 | 8/1978 | Germany . |
| 61-26008 | 2/1986 | Japan . |
| 62-120308 | 6/1987 | Japan . |
| 1-93562 | 4/1989 | Japan . |
| WO 83/01571 | 5/1983 | WIPO . |
| WO 92/08685 | 5/1992 | WIPO . |

OTHER PUBLICATIONS

Francis Szoka, Jr. et al, "Procedure for Preparation of Liposomes With Large Internal Aqueous Space and High capture by Reverse–Phase Evaporation", Proc. Natl. Acad. Sci. USA, vol. 75, No. 9, Sep. 1978, pp. 4194–4198.
English Language Derwent Abstract of DE 2 703 185., 1978.
English Language Derwent Abstract of EP 0 383 024., 1990.
English Language Derwent Abstract of EP 0 500 437., 1992.
English Language Derwent Abstract of EP 0 647 617, 1995.
English Language Derwent Abstract of FR 2 091 516, 1972.
English Language Derwent Abstract of FR 2 315 991, 1977.
English Language Derwent Abstract of FR 2 465 780., 1981.
English Language Derwent Abstract of FR 2 482 128., 1981.
Patent Abstracts of Japan, vol. 013, No. 308, Jul. 14, 1989 (JP 01 93562).

*Primary Examiner*—Shailendra Kumar
*Attorney, Agent, or Firm*—Finnegan, Henderson, Farabow, Garrett & Dunner, L.L.P.

[57] ABSTRACT

The present application relates to novel ceramide compounds to their process of preparation and to their use in cosmetics or in pharmaceuticals, in particular for treating and caring for the skin, hair, nails and eyelashes.

4 Claims, No Drawings

CERAMIDE COMPOUND, PROCESS OF PREPARATION AND USE

The present invention relates to novel compounds of ceramide type, their process of preparation and their use, in particular for the treatment and care of the skin, hair, nails and eyelashes, in cosmetics or in pharmaceuticals.

Exposure of the skin to the cold, to the sun or to atmospheres with a low relative humidity, repeated treatments with washing compositions or contact with organic solvents are factors which result in a visible drying to various degrees. The skin appears drier and less supple and the skin contours appear more pronounced. Furthermore, hair which is subjected too often to certain hair treatments loses its glossy appearance and can become coarse and brittle.

Provision has in particular been made to use ceramides in order to solve these problems. This is because it is known that these compounds are the major constituents of the intercorneocytic lipids of the stratum corneum and participate in maintaining the integrity of the cutaneous barrier.

The ceramides used in cosmetics are generally natural extracts derived in particular from pigskin, ox brain, eggs, blood cells, plants, such as wheat, and the like (See Japanese Patent Applications J86/260008 and J87/120308). Such ceramides have also been provided for the protection of hair (See EP 0,278,505).

They are therefore always mixtures with a greater or lesser content of ceramides, the composition of which is difficult to monitor. In addition, these mixtures are subject to bacterial contamination. It is thus difficult to control or preserve them. When they are of animal origin, there is in addition a risk of contamination by the agent responsible for BSE (bovine spongiform encephalopathy).

Provision has been made, in order to overcome these disadvantages, for synthetic ceramides, in particular in European Patent Applications EP 500,437 and EP 647,617. These compounds, used in cosmetic or dermatological compositions for the treatment and care of the skin and hair, have a moisturizing effect which makes it possible to prevent or to correct certain effects of visible drying of the skin or hair.

Provision has also been made, in European Patent Application EP 420,722, for lipid ceramide derivatives corresponding to the formula:

in which $R^1$ denotes a $C_{11}$ to $C_{21}$ alkyl or alkenyl radical and $R^2$ denotes a $C_8$ to $C_{30}$ hydrocarbon-comprising radical. In this document, provision has been made to modify the amide junction of the ceramides by replacing it by a urethane junction. The compounds thus obtained are of particular advantage in the treatment of the skin or hair and also make it possible to prevent or to correct certain effects of drying. Furthermore, they exhibit a weak aggressive nature with respect to the skin or ocular mucous membranes and good emollient and softening properties.

However, the need still remains to have available compounds which have an improved moisturizing and/or treating effect with respect to the compounds of the prior art, while being capable of application in the cosmetic and/or dermatological fields, in particular.

The inventors have thus sought compounds which make it possible to prevent or to correct phenomenona which are reflected by a visible drying and which restore the skin's suppleness and the hair's gloss and softness.

The subject-matter of the present invention is thus compounds corresponding to the formula (I):

in which:

$R^1$ denotes a saturated or unsaturated, linear or branched, $C_9$ to $C_{23}$ alkyl radical which may be optionally hydroxylated, $R^2$ denotes hydrogen or a saturated or unsaturated, linear or branched, $C_1$ to $C_8$ alkyl radical, $R^3$ denotes a saturated or unsaturated, linear or branched, $C_1$ to $C_{32}$ alkyl radical which may be optionally hydroxylated, it being possible for the hydroxyl radical itself to be substituted by a saturated or unsaturated, linear or branched, $C_1$ to $C_{24}$ acyl radical; the $R^3$ group can optionally be interrupted by 1 to 7 heteroatoms.

Another subject of the invention is a process for the preparation of the above compounds, in which an aminodiol of formula:

is reacted with an azolide derivative in an inert solvent, so as to obtain the desired compound.

Another subject of the invention is an aqueous dispersion of lipid spherules composed of organized molecular layers enclosing an encapsulated aqueous phase, the layers being composed of at least one compound of formula (I) above in combination with at least one other lipid compound.

Another subject of the invention is a composition, in particular for cosmetic or pharmaceutical use, comprising, in a cosmetically or pharmaceutically acceptable medium, at least one compound of formula (I) and/or one aqueous dispersion of lipid spherules as above.

Another subject of the invention is the use of a compound of formula (I) or of an aqueous dispersion of lipid spherules comprising it as moisturizing, emollient and/or softening agent.

Yet another subject of the invention is the use, in cosmetics or in pharmaceuticals, of a compound of formula (I) or of an aqueous dispersion of lipid spherules comprising it for treating and/or caring for the skin and/or keratinous substances, in particular for treating and/or caring for damaged and/or aged skin and/or of damaged hair and/or nails.

It has been found that these novel compounds exhibit a very good moisturizing power for the skin and/or keratinous substances (hair, eyelashes, eyebrows and nails). They can be used with very particular advantage when an effect in combating drying of the skin and/or of the hair is sought in cosmetics or in pharmaceuticals.

These novel compounds have the advantage of improving and/or of reestablishing the barrier function when they are applied to the skin. Furthermore, these compounds exhibit a weak aggressive nature with respect to the skin or ocular mucous membranes and good tolerance with respect to cell membranes, such as those of erythrocytes.

These novel compounds exhibit emollient and softening properties, in particular for the skin and hair. In addition, they can be easily dissolved in the fatty phases of cosmetic or pharmaceutical compositions.

The compounds according to the invention can be used to treat damaged and/or aged skin and damaged hair or nails in the cosmetic or pharmaceutical field.

Hair treated with these compounds of formula (I) exhibits a glossy appearance, a softer feel and a reduced sensitivity to water, due to the contribution of lipid matter uniformly distributed over the scales of the hair. The mechanical and liveliness (i.e., body) properties are also improved.

The compounds according to the invention thus correspond to the following formula:

$R^1$—CHOH—CH(CH$_2$OH)—NH—CO—NR$^2$R$^3$ where
$R^1$ preferably denotes an optionally hydroxylated, saturated or unsaturated, linear $C_{11}$ to $C_{19}$ alkyl radical,
$R^2$ preferably denotes hydrogen, and
$R^3$ preferably denotes a saturated or unsaturated, linear or branched, $C_4$ to $C_{18}$ alkyl radical which can be interrupted by 1 to 5 heteroatoms.

Mention may be made, among heteroatoms, of oxygen, nitrogen and/or silicon.

The compounds according to the invention can be used in the form of a pure isomer or of mixtures of isomers.

The preferred compounds according to the invention are:
2-(N-hexadecylureido)octadecane-1,3-diol,
2-(N-ethyloxycarbonylmethylureido)octadecane-1,3-diol,
2-(N-oleylureido)octadecane-1,3-diol,
N-(2-aminooctadecane-1,3-diol)carboxy-N'-aminopropylsiloxane, and
2-(N-dodecylureido)octadecane-1,3-diol.

The compounds according to the invention can be easily prepared by a person skilled in the art, in particular using the process which is the subject-matter of the invention. This process comprises reacting an aminodiol of formula:

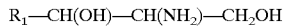

$R_1$—CH(OH)—CH(NH$_2$)—CH$_2$OH with an azolide derivative in an inert solvent, so to obtain the desired compound.

Use is preferably made of an imidazolide derivative, such as an imidazolidide.

The two starting constituents are preferably added in equimolar amounts.

The reaction is preferably carried out under hot conditions, at reflux, for 1 to 5 hours, preferably 2 to 4 hours.

The inert solvent is preferably an organic solvent, such as an alcohol or an ether.

The reaction mixture can, after reaction, be poured into a bath of ice-cold water, so as to precipitate the desired compound.

The compound of formula (I) can subsequently, in the usual way, be filtered, washed and dried and then, optionally, recrystallized.

The compounds according to the invention can thus have various applications, in particular in cosmetic or pharmaceutical compositions.

Thus, the compositions comprising the compounds according to the invention can comprise, in addition to the compound or compounds of formula (I), a cosmetically or pharmaceutically acceptable medium.

These compositions can be provided in the form of emulsions (milk or cream), of aqueous/alcoholic, oily or oleoalcoholic lotions, of gels, of solid to sticks or dispersions, or of aerosol foam or sprays. These compositions are, for example, emollient lotions, milks or creams; milks or creams for caring for the skin or hair; make-up removal creams, lotions or milks; foundation bases; anti-sun or after-sun lotions, milks or creams; artificial tanning lotions, milks or creams; shaving creams or foams; aftershave lotions; shampoos; lip rouges; optionally treating mascaras; nail varnishes or nail care products.

These compositions can also be provided in the form of lipsticks, intended either to colour the lips or to avoid chapping, or of make-up products for the eyes or of rouges and foundations for the face.

The pharmaceutical dosage form and the amount of compound present in the composition can be easily determined by a person skilled in the art on the basis of his broad knowledge.

By way of indication, the compound of formula (I) can be present in an amount of 0.001 to 20% by weight with respect to the total weight of the composition, preferably in a proportion of 0.01 to 10% by weight.

When the compositions according to the invention are provided in the form of emulsions of water-in-oil or oil-in-water type, the fatty phase is preferably composed essentially of a mixture of compounds of formula (I) with at least one oil, and optionally one other fatty substance.

The fatty phase of the emulsions can constitute from 5 to 60% of the total weight of the emulsion. The aqueous phase of the emulsions preferably constitutes from 30 to 85% of the total weight of the emulsion. The proportion of emulsifying agent can range from 1 to 20% and preferably from 2 to 12% of the total weight of the emulsion.

When the compositions according to the invention are provided in the form of oily, oleoalcoholic or aqueous/alcoholic lotions, they can constitute, for example, anti-sun lotions comprising a screening agent which absorbs UV rays or skin-softening lotions; the oily lotions can additionally constitute foaming oils comprising an oil-soluble surfactant, bath oils, and the like.

Mention may be made, among the main adjuvants which can be present in the compositions according to the invention, of fatty substances, such as mineral, animal or vegetable oils or waxes, fatty acids, fatty acid esters, such as fatty acid triglycerides having from 6 to 18 carbon atoms, or fatty alcohols; emulsifying agents, such as oxyethylenated fatty alcohols or polyglycerol alkyl ethers; solvents, such as lower monoalcohols or polyalcohols comprising from 1 to 6 carbon atoms, or water.

The monoalcohols or polyalcohols which are more particularly preferred are chosen from ethanol, isopropanol, propylene glycol, glycerol and sorbitol.

Mention may be made, by way of fatty substances, among mineral oils, of petrolatum; among animal oils, of whale, shark, seal, menhaden, halibut liver, cod, tuna, tortoise, ox hoof, horse hoof, sheep hoof, mink, otter or marmot oils and the like; among vegetable oils, of almond, wheat germ, olive, maize germ, jojoba, sesame, sunflower, palm, walnut, karite, shorea, macadamia or blackcurrant seed oils and the like.

Use may be made, among fatty acid esters, of esters of saturated or unsaturated $C_{12}$ to $C_{22}$ acids and of lower alcohols, such as isopropanol or glycerol, or of saturated or unsaturated, linear or branched, $C_8$ to $C_{22}$ fatty alcohols or alternatively of $C_{10}$–$C_{22}$ 1,2-alkanediols.

Mention may also be made, as fatty substances, of petrolatum, paraffin, lanolin, hydrogenated lanolin, tallow, acetylated lanolin or silicone oils.

Mention may be made, among waxes, of Sipol wax, lanolin wax, beeswax, candelilla wax, microcrystalline wax, carnauba wax, spermaceti, cocoa butter, karite butter, silicone waxes, hydrogenated oils which are solid at 25° C., sucroglycerides, or calcium, magnesium and aluminium oleates, myristates, linoleates and stearates.

Mention may be made, among fatty alcohols, of lauryl, cetyl, myristyl, stearyl, palmityl or oleyl alcohols and Guerbet alcohols, such as 2-octyldodecanol, 2-decyltetradecanol or 2-hexyldecanol.

Mention may be made, by way of emulsifying agents, among polyoxyethylenated fatty alcohols, of lauryl, cetyl, stearyl and oleyl alcohols comprising from 2 to 20 mol of ethylene oxide and, among polyglycerol alkyl ethers, of $C_{12}$–$C_{18}$ alcohols comprising from 2 to 10 mol of glycerol.

It can also be useful to use thickening agents, such as cellulose derivatives, polyacrylic acid derivatives, guar gum, locust bean gum or xanthan gum.

The compositions according to the invention can also comprise adjuvants commonly used in cosmetics or in pharmaceuticals and in particular moisturizing products, softeners, products for treating skin complaints, sunscreen agents, germicides, cosmetic or pharmaceutical active principles, colorants, preservatives, fragrances and propellants.

When the compositions according to the invention are dispersions, they can be dispersions of compounds of formula (I) in water in the presence of surfactant or alternatively aqueous dispersions of lipid spherules composed of organized molecular layers enclosing an encapsulated aqueous phase, it being possible for these layers to be composed of at least one compound of formula (I) in combination with at least one other lipid compound. This is because it has been found that the compounds of formula (I), in combination with other lipids, could be used for the formation of lipid spherules.

Mention may be made, to this end, as lipid compounds, of long-chain alcohols and diols, sterols, such as cholesterol, phospholipids, cholesteryl sulphate, cholesteryl phosphate, long-chain amines and their quaternary ammonium derivatives, dihydroxyalkylamines, polyoxyethylenated fatty amines, long-chain aminoalcohol esters, their salts and quaternary ammonium derivatives, phosphoric esters of fatty alcohols, such as dicetyl hydrogen phosphate or its sodium salt, alkyl sulphates, such as sodium cetyl sulphate, fatty acids in the form of salts, or lipids of the type of those disclosed in Patent Applications FR 2,315,991, FR 1,477,048, FR 2,091,516, WO 83/01571 and WO 92/08685, the disclosures of which are hereby incorporated by reference in their entirety.

Use may be made, for example, as other lipids, of lipids comprising a saturated or unsaturated, linear or branched, lipophilic chain comprising 12 to 30 carbon atoms, for example an oleyl, lanolyl, tetradecyl, hexadecyl, isostearyl, lauryl or alkylphenyl chain.

The hydrophilic group of these lipids can be an ionic or non-ionic group. Mention may be made, by way of non-ionic groups, of groups derived from polyethylene glycol. Use may also advantageously be made, as lipids forming the lamellar phase, of polyglycerol ethers, such as those disclosed in French Patents Nos. 1,477,048, 2,091,516, 2,465, 780 and 2,482,128, the disclosures of which are hereby incorporated by reference in their entirety.

Use may advantageously be made, by way of ionic group, of a group derived from an amphoteric, anionic or cationic compound.

Other lipids disclosed in International Patent Application WO 83/01571, the disclosure of which is hereby incorporated by reference in its entirety, as being able to be used for the formation of vesicles are glycolipids, such as lactosylceramide, galactocerebroside, gangliosides and trihexosylceramide, and phospholipids, such as phosphatidylglycerol and phosphatidylinositol.

It is thus possible to obtain a dispersion of lipid spherules composed of organized molecular layers of compound of formula (I) and of lipid as defined above including an aqueous phase to be encapsulated.

The dispersed spherules generally have a diameter ranging from 0.05 μm to 5 μm.

The continuous phase of the dispersion which surrounds the spherules is an aqueous phase.

The aqueous phase encapsulated in the spherules can be water or an aqueous solution of active substance and, in this case, is preferably isoosmotic with respect to the continuous phase of the dispersion.

The spherules can be obtained in particular according to the process disclosed in Patent FR 2,315,991, the disclosure of which is hereby incorporated by reference in its entirety, according to which a dispersion of spherules, composed of organized molecular layers including an aqueous phase to be encapsulated, is prepared by bringing into contact, on the one hand, at least one compound of formula (I) in combination with one or more lipids and, on the other hand, the aqueous phase to be encapsulated in these spherules, by stirring in order to ensure mixing and to obtain a lamellar phase, by subsequently adding a dispersion liquid in an amount greater than the amount of lamellar phase obtained, and by vigorously shaking for a period of time ranging from 15 minutes to 3 hours approximately.

Another preparation process which can be used in the present invention is the process called REV (reverse-phase evaporation vesicle), described in Proc. Natl. Acad. Sci. USA., Vol. 75, No. 9, pages 4194–4198 (1978), by Szoka and Papahadjopoulos, the disclosure of which is hereby incorporated by reference in its entirety.

Use may also be made of the process which comprises the sequence of stages including dissolving at least one lipid in at least one water-immiscible organic solvent; in adding the organic phase thus obtained to an aqueous phase; in forming a dispersion of the two phases with vigorous stirring, it being possible for the size of the vesicles to be adjusted by varying the stirring speed during this phase mixing; in then evaporating the solvent(s) with vigorous stirring; and, if appropriate, in concentrating the dispersion.

The active substances which can be present in the encapsulated aqueous phase can be substances of pharmaceutical or food interest or substances having a cosmetic activity. When they are water-soluble, they are in the aqueous phase encapsulated inside the vesicles.

The water-soluble substances having a cosmetic and/or pharmaceutical activity can be products intended for caring for or treating the skin and hair, such as, for example, humectants, such as glycerol, sorbitol, pentaerythritol or pyrrolidonecarboxylic acid and its salts; artificial tanning agents, such as dihydroxyacetone, erythrulose, glyceraldehyde or γ-dialdehydes, such as tartaric aldehyde, these compounds optionally being used in combination with colorants; water-soluble sunscreen agents; antiperspirants, deodorants, astringents, freshening, tonic, cicatrizing, keratolytic or depilatory products, or scented waters; plant tissue extracts, such as polysaccahrides; water-soluble colorants; antidandruff agents; antiseborrhoeic agents; oxidizing agents, such as bleaching agents, for example aqueous hydrogen peroxide solution; or reducing agents, such as thioglycolic acid and its salts.

Mention may also be made of vitamins, hormones, enzymes, such as superoxide dismutase, vaccines, antiinflammatory agents, such as hydrocortisone, antibiotics, bactericides or cytotoxic or antitumour agents.

When the active substances are liposoluble, they are found incorporated within the lamellae of the vesicles. They can be chosen from the group formed by liposoluble sunscreen agents, substances intended to improve the state of dry or senile skin, tocopherols, vitamins E, F or A and their esters, retinoic acid, antioxidants, essential fatty acids, glycyrrhetinic acid, keratolytic agents and carotenoids.

The dispersions of lipid spherules exhibit the advantage of conveying active substances, which are thus masked and protected with respect to various degrading agents: oxidizing agents and more generally compounds which are reactive with respect to encapsulated active substances. The penetration and the fixing of the active substances can be modulated by varying the size of the spherules and their electric charge. The action of these active substances can also be deferred in this way (delay effect).

These aqueous dispersions of spherules composed of organized molecular layers of compounds of formula (I) in combination with other lipids including an aqueous phase to be encapsulated can be used in particular in the cosmetic or pharmaceutical fields, in particular for treating and/or caring for the skin and keratinous substances, such as the hair, eyelashes, eyebrows and nails.

They can be used as is or introduced into a cosmetic or pharmaceutical composition.

The invention is illustrated in more detail in the following examples.

EXAMPLES OF THE PREPARATION OF COMPOUNDS ACCORDING TO THE INVENTION

The compounds according to the invention can be prepared by reacting the following constituents:

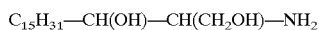

$C_{15}H_{31}$—CH(OH)—CH(CH$_2$OH)—NH$_2$ and

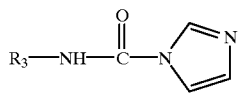

so as to obtain a compound according to the invention in which:
$R_1$ is a saturated alkyl radical having 15 carbon atoms,
$R_2$ is hydrogen.

The general procedure comprises adding one equivalent of imidazolide derivative (conventionally prepared by reaction of carbonyl-diimidazole with an amine) and one equivalent of 2-aminooctadecane-1,3-diol dissolved in the minimum amount of isopropanol. The reaction mixture is heated at reflux for 3 hours and is then poured into a bath of ice-cold water. The desired compound precipitates. It is filtered off, washed and dried and then, optionally, recrystallized from ethanol.

Example 1

Preparation of 2-(N-hexadecylureido)octadecane-1,3-diol

The $R_3$ radical is a —$C_{16}H_{33}$ radical.
After filtration, drying and recrystallization, a white solid was obtained with a yield of 76%.
Melting point: approximately 92° C.
Elemental analysis:

|  | C | H | N | O |
|---|---|---|---|---|
| % calculated | 73.89 | 12.76 | 4.92 | 8.44 |
| % found | 74.07 | 12.73 | 4.83 | 8.22 |

The elemental analysis of the product obtained is in accordance with the expected product.

Example 2

Preparation of 2-(N-dodecylureido)octadecane-1,3-diol

The $R_3$ radical is a —$C_{12}H_{25}$ radical.
After filtration, drying and recrystallization, a white solid was obtained with a yield of 57%.
Melting point: approximately 81.8° C.
Elemental analysis:

|  | C | H | N | O |
|---|---|---|---|---|
| % calculated | 72.60 | 12.58 | 5.46 | 9.36 |
| % found | 72.00 | 12.29 | 5.51 | 9.78 |

The elemental analysis of the product obtained is in accordance with the expected product.

Example 3

Preparation of 2-(N-ethyloxycarbonylmethylureido)octadecane-1,3-diol

The $R_3$ radical is a —$CH_2$—COO—$C_2H_5$ radical.
After filtration and drying, a solid compound was obtained with a yield of 76%.
Elemental analysis:

|  | C | H | N | O |
|---|---|---|---|---|
| % calculated | 64.15 | 10.77 | 6.51 | 18.58 |
| % found | 61.84 | 10.79 | 6.52 | 17.78 |

The elemental analysis of the product obtained is in accordance with the expected product.

Example 4

Preparation of N-(2-aminooctadecane-1,3-diol) carboxy-N'-aminopropylsiloxane

The $R_3$ is a

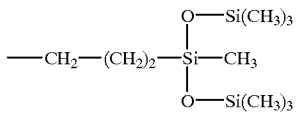

radical.
After filtration and drying, a white solid was obtained with a yield of 85%.
Elemental analysis:

|  | C | H | N | O | Si |
|---|---|---|---|---|---|
| % calculated | 57.37 | 10.96 | 4.61 | 13.18 | 13.88 |
| % found | 57.85 | 10.89 | 4.89 | — | 13.40 |

The elemental analysis of the product obtained is in accordance with the expected product.

Example 5

Preparation of 2-(N-oleylureido)octadecane-1,3-diol

The $R_3$ radical is a —$CH_2$—$C_7H_{14}$—CH=CH—$C_8H_{17}$ radical.

After filtration, drying and recrystallization, a solid white compound was obtained with a yield of 51%.

Elemental analysis:

|  | C | H | N | O |
|---|---|---|---|---|
| % calculated | 74.69 | 12.54 | 4.71 | 8.07 |
| % found | 72.94 | 12.70 | 4.71 | 8.04 |

The elemental analysis of the product obtained is in accordance with the expected product.

Example 6

Measurement of the Imperceptible Water Loss (IWL)

This measurement was made using an evaporimeter (Servomed) which quantitatively determines the evaporation of water, that is to say diffusional water transportation, from a sample of stratum corneum, delipidated beforehand, sealing a cylindrical capsule comprising water, the entire assembly being placed in a chamber at controlled relative temperature and controlled relative humidity. Sensors make it possible to measure the partial vapour pressure of water at two points situated at different distances from the sample. The partial vapour pressure of water gradient between the two points is thus determined and thus the rate of evaporation in accordance with Fick's law.

A comparative test was carried out on the effects on the IWL of a 1% solution of the test compound in a dichloromethane/methanol solvent mixture in a 2/1 proportion. The test was carried out at 30° C. and under a relative humidity of 40%.

The compounds tested were:

Compound A: 2-(N-hexadecylureido)octadecane-1,3-diol (Example 1 of the invention)

Compound B: N-hexadecyloxycarbonyl-2-aminooctadecane-1,3-diol (Example 2 of EP 420,722).

The results are combined in the following table.

| Compound | Concentration | IWL at 20 hours (%) |
|---|---|---|
| Compound A | 1% | −26 ± 2 |
| Compound B | 1% | −16 ± 4 |

It was thus found that the application of the compounds according to the invention made it possible to significantly reduce the evaporation of the water present in the stratum corneum, thereby demonstrating the improved barrier properties, for the compounds according to the invention, to permeability to stratum corneum water.

Example 7

Conditioner Composition

A conditioner for caring for or treating the hair was prepared using the following constituents:

| Cetylstearyl alcohol | 2.5 g |
|---|---|
| Myristyl/cetyl/stearyl myristate/palmitate/stearate mixture | 0.5 g |
| Behenyltrimethylammonium chloride, at 80% in a water/isopropanol mixture (Catinal DC 80 from Toho) | 0.6 g |
| PDMS with aminoethylaminopropyl groups, as a 35% emulsion in water (DC939 from Dow Corning) | 4 g |
| Compound of Example 1 | 0.6 g |
| Preservatives, fragrance | q.s. |
| Water | q.s. for 100 g |

Example 8

Shampoo Composition

A shampoo for caring for or treating the hair was prepared using the following constituents:

| Sodium lauryl ether sulphate | 16 g AM |
|---|---|
| Cocoylbetaine | 2.5 g AM |
| Hydroxypropylcellulose crosslinked with epichlorohydrin, quaternized with trimethylamine | 0.2 g |
| Compound of Example 1 | 0.1 g |
| Preservatives, fragrance | q.s. |
| HCl | q.s. pH 6.5 |
| Water | q.s. for 100 g |

Example 9

Shampoo Composition

A shampoo for caring for or treating the hair was prepared using the following constituents:

| Sodium lauryl ether sulphate | 16 g AM |
|---|---|
| Cocoylbetaine | 2.5 g AM |
| Hydroxypropylcellulose crosslinked with epichlorohydrin, quaternized with trimethylamine | 0.2 g |
| Compound of Example 2 | 0.1 g |
| Preservatives, fragrance | q.s. |
| HCl | q.s. pH 6.5 |
| Water | q.s. for 100 g |

Example 10

Oil for Caring for the Body

A moisturizing oil for dry skin was prepared using the following constituents:

| Caprylic/capric triglycerides | 6.5 g |
|---|---|
| Propylene glycol dicaprylate/dicaprate | 22 g |
| Cetearyl octanoate and isopropyl myristate | 5 g |
| Isostearyl neopentanoate | 2.5 g |
| Groundnut oil | 5.25 g |
| Compound of Example 5 | 1.5 g |
| Antioxidant, preservatives, fragrance | q.s. |
| Cyclomethicone | q.s. for 100 g |

Example 11

Cream for Caring for the Face

A moisturizing care cream for normal skin and combination skin was prepared using the following constituents:

| | |
|---|---|
| Petrolatum | 4 g |
| Hydrogenated polyisobutene | 6.5 g |
| Cetyl alcohol | 2.7 g |
| Sorbitan tristearate | 0.5 g |
| PEG 40 stearate | 3.2 g |
| Myristyl myristate | 3 g |
| Glyceryl stearate | 3 g |
| Karite butter | 2 g |
| Cyclomethicone | 5 g |
| Stearic acid | 0.2 g |
| Sodium hydroxide | 0.5 g |
| Sodium citrate | 0.1 g |
| Compound of Example 1 | 1 g |
| Antioxidant, preservatives, fragrance | q.s. |
| Water | q.s. for 100 g |

Example 12

Nourishing Cream for the Face

A care cream for dry skin and combination skin was prepared using the following constituents:

| | |
|---|---|
| Cetyl dimethicone copolyol | 2.5 g |
| Polyglyceryl-4 isostearate | 1.5 g |
| Isoparaffin | 10 g |
| Apricot kernel oil | 5 g |
| Cyclomethicone | 8 g |
| Acetylated glycol stearate and tristearin | 1 g |
| Glycerol | 5 g |
| Magnesium sulphate | 0.7 g |
| Aluminium starch octenylsuccinate | 3 g |
| Compound of Example 3 | 1 g |
| Antioxidant, preservatives, fragrance | q.s. |
| Water | q.s. for 100 g |

Example 13

Cream for Caring for the Face

A day cream was prepared using the following constituents:

| | |
|---|---|
| Sucrose stearate | 5 g |
| Methyl glucose sesquistearate | 2.5 g |
| Apricot kernel oil | 11 g |
| Stearic acid | 1 g |
| Gelling agent | 0.4 g |
| Cyclomethicone | 9 g |
| Isopropyl isostearate | 5 g |
| Compound of Example 1 | 1 g |
| Antioxidant, preservatives, fragrance | q.s. |
| Water | q.s. for 100 g |

Example 14

Cream for Caring for the Face

A moisturizing care cream was prepared using the following constituents:

| | |
|---|---|
| Sorbitan tristearate | 0.25 g |
| PEG 40 stearate | 4 g |
| Cetyl alcohol | 1.5 g |
| Myristyl myristate | 2 g |
| Glyceryl stearate | 3 g |
| Octyl palmitate | 2 g |
| Hydrogenated polyisobutene | 13.5 g |
| Cyclomethicone | 10 g |
| Glycerol | 6 g |
| Compound of Example 2 | 0.8 g |
| Antioxidant, preservatives, fragrance | q.s. |
| Water | q.s. for 100 g |

What is claimed is:

1. A compound corresponding to the formula (I):

$$R^1\text{---}CH(OH)\text{---}CH(CH_2OH)\text{---}NH\text{---}CO\text{---}NR^2R^3$$

in which:

$R^1$ denotes a saturated or unsaturated, linear or branched, $C_9$ to $C_{23}$ alkyl radical which may be optionally hydroxylated, $R^2$ denotes hydrogen or a saturated or unsaturated, linear or branched, $C_1$ to $C_8$ alkyl radical, and $R^3$ denotes a saturated or unsaturated, linear or branched, $C_1$ to $C_{32}$ alkyl radical which may be optionally hydroxylated, it being possible for said hydroxyl radical itself to be substituted by a saturated or unsaturated, linear or branched, $C_1$ to $C_{24}$ acyl radical; $R^3$ can optionally be interrupted by 1 to 7 heteroatoms.

2. A compound according to claim 1, in which the $R^1$ radical denotes a saturated or unsaturated, linear $C_{11}$ to $C_{19}$ alkyl radical which may be optionally hydroxylated; and/or the $R^2$ radical denotes hydrogen; and/or the $R^3$ radical denotes a saturated or unsaturated, linear or branched, $C_4$ to $C_{18}$ alkyl radical which can be interrupted by 1 to 5 heteroatoms.

3. A compound according to claim 1, wherein said compound is:

2-(N-hexadecylureido)octadecane-1,3-diol, 2-(N-ethyloxycarbonylmethylureido)octadecane-1,3-diol, 2-(N-oleylureido)octadecane-1,3-diol, N-(2-aminooctadecane-1,3-diol)carboxy-N'-aminopropylsiloxane, or 2-(N-dodecylureido)octadecane-1,3-diol.

4. A process for the preparation of a compound according to claim 1, comprising:

reacting an aminodiol of formula:

$$R_1\text{---}CH(OH)\text{---}CH(NH_2)\text{---}CH_2OH$$

with an azolide derivative in an inert solvent to obtain the desired compound.

* * * * *

UNITED STATES PATENT AND TRADEMARK OFFICE
CERTIFICATE OF CORRECTION

PATENT NO.: 6,077,972
DATED: June 20, 2000
INVENTOR(S): Rémy TULOUP et al.

It is certified that an error appears in the above-identified patent and that said Letters Patent is hereby corrected as shown below:

TITLE:

Front page, line 1, change "COMPOUND" to --COMPOUNDS--.

IN THE ABSTRACT:

Front page, in lines 1-2 of the Abstract, replace "compounds to" with --compounds, to--.

Signed and Sealed this

Third Day of April, 2001

*Attest:*

NICHOLAS P. GODICI

*Attesting Officer*     Acting Director of the United States Patent and Trademark Office